US012624346B2

(12) United States Patent
Kim et al.

(10) Patent No.: US 12,624,346 B2
(45) Date of Patent: May 12, 2026

(54) VACUUM DRYING METHOD FOR BOTULINUM TOXIN

(71) Applicant: PROTOX INC., Gyeonggi-do (KR)

(72) Inventors: Hak Kun Kim, Gyeonggi-do (KR); Jin Hee Ahn, Seoul (KR); Seul Gi Kwon, Seoul (KR)

(73) Assignee: PRO-TOX INC., Gyeonggi-Do (KR)

( * ) Notice: Subject to any disclaimer, the term of this patent is extended or adjusted under 35 U.S.C. 154(b) by 420 days.

(21) Appl. No.: 18/029,787

(22) PCT Filed: Oct. 7, 2021

(86) PCT No.: PCT/KR2021/013828
§ 371 (c)(1),
(2) Date: Mar. 31, 2023

(87) PCT Pub. No.: WO2022/075785
PCT Pub. Date: Apr. 14, 2022

(65) Prior Publication Data
US 2023/0365957 A1 Nov. 16, 2023

(30) Foreign Application Priority Data
Oct. 7, 2020 (KR) ........................ 10-2020-0129385

(51) Int. Cl.
*F26B 5/04* (2006.01)
*C12N 9/52* (2006.01)
*C12N 9/96* (2006.01)

(52) U.S. Cl.
CPC ................. *C12N 9/52* (2013.01); *C12N 9/96* (2013.01); *C12Y 304/24069* (2013.01); *F26B 5/04* (2013.01)

(58) Field of Classification Search
None
See application file for complete search history.

(56) References Cited

U.S. PATENT DOCUMENTS

2005/0112146 A1 5/2005 Graham
2010/0291136 A1 11/2010 Jung et al.

FOREIGN PATENT DOCUMENTS

| EP | 1366771 A2 | 12/2003 |
| KR | 101087017 B1 | 12/2011 |
| KR | 1020130133767 A | 12/2013 |
| KR | 1020170133530 A | 12/2017 |
| WO | 2007016018 A2 | 2/2007 |

OTHER PUBLICATIONS

Pikal et al. (International Journal of Pharmaceutics, vol. 60, pp. 203-217, 1990).*
International Search Report dated Jan. 24, 2022 for corresponding International Application PCT/KR2021/013828, 15 pages (with English Translation).
Pisal et al., "Vacuum foam drying for preservation of lasota virus: Screening of foaming agent and cycle optimization", Indian Journal of Biotechnology, vol. 5, Oct. 2006, pp. 491-497.

* cited by examiner

*Primary Examiner* — Richard G Hutson
(74) *Attorney, Agent, or Firm* — MH2 Technology Law Group, LLP

(57) ABSTRACT

The present invention relates to a vacuum drying method for botulinum toxin, and specifically to a vacuum drying method for botulinum toxin, comprising the steps of: a) first drying of a solution containing botulinum toxin at a temperature of 5° C. to 30° C. under a pressure of 0.01 to 2 mmHg; b) a second drying of the first-dried product obtained in step a) at a temperature of 5° C. to 20° C. under a pressure of 0.01 to 1 mmHg; and c) final drying of the second-dried product obtained in step b) at a temperature of 5° C. to 30° C. under a pressure of 0.01 to 0.5 mmHg. The present invention can advantageously improve yield, stability and manufacturing efficiency, compared to conventional methods for vacuum drying botulinum toxin by freeze-drying.

14 Claims, 2 Drawing Sheets

VACUUM DRYING METHOD FOR BOTULINUM TOXIN

CROSS-REFERENCE TO RELATED APPLICATIONS

This application is a national stage application of PCT/KR2021/013828 filed 7 Oct. 2021 which claims priority to Korean Patent Application No. 10-2020-0129385 filed 7 Oct. 2020. The entire disclosures of each application are herein incorporated by reference.

TECHNICAL FIELD

The present invention relates to a drying process in a process of manufacturing a botulinum toxin preparation, and specifically to a vacuum drying method for botulinum toxin that dries by vacuum drying and not by conventional freeze drying, which exhibits improved yield, stability and manufacturing efficiency compared to conventional methods.

BACKGROUND ART

It is known that botulinum toxin is a neurotoxic protein produced by *Clostridium botulinum* and related species and has an effect of blocking the release of acetylcholine, a neurotransmitter secreted from the axon terminal of a neuromuscular junction. In addition, there are 8 types of serologically related natural botulinum toxin from type A to type H, and botulinum toxin has varying effects on the human body depending on the type, but is known to have a fatal effect on the human body as a whole. In the case of botulinum toxin type H, injection of only one over two billion of a gram into the body can be lethal, and botulinum toxin types A and B can cause diseases. Botulinum toxin type A has been used for strabismus correction after safety and efficacy were proven since 1978. Further, it was discovered that wrinkles in the glabellar area disappeared after injecting the toxin for the treatment of blepharospasm patients in 1987, and the toxin attracted interest as a possibility of a use for cosmetic purposes. In general, botulinum toxin types A and B are manufactured into medicine and medical supplies and injected intramuscularly as an injection to treat muscle spasms and diseases caused by muscle overactivity. Considering the effect on the human body according to the injection amount, guidelines for the use of botulinum toxin and guidelines for the approval of botulinum toxin have been prepared.

Currently, there are problems such as instability of protein and loss of active ingredients in the process of preparing medicine with botulinum toxin, so a separate ingredient such as a stabilizer is required. In this regard, Korean Patent Registration No. 10-1087017 discloses a method for manufacturing a liquid composition by using polysorbate 20, methionine and/or isoleucine.

Commercially available botulinum toxin preparations are distributed in powder form after freeze drying or vacuum drying for preventing decomposition of botulinum toxin preparations, facilitating handling of botulinum toxin preparations, and reducing transportation costs or the like and can be reconstituted by using a liquid carrier such as water or saline solution before use.

However, in the case of freeze drying, which is a drying technique commonly used in the related art, there are disadvantages in that botulinum toxin is lost due to the instability thereof and that it takes a long period of time for freeze drying. Accordingly, the present inventors have diligently studied to improve a drying method for botulinum toxin and resultantly found a vacuum drying method, in which the loss of active materials is small and the required time is significantly shortened while properties of the product are excellent, by applying the vacuum drying according to the present invention consisting of specific steps, to complete the present invention.

SUMMARY OF INVENTION

Technical Problem

The present invention is to provide a vacuum drying method for botulinum toxin in which yield, stability, manufacturing efficiency, and productivity are significantly improved by vacuum drying, in order to solve the problems in terms of production efficiency in that it takes a long period of time for drying and of yield problem after drying of the botulinum toxin when botulinum toxin is manufactured by a method for drying botulinum toxin by freeze drying in the related art.

Solution to Problem

In order to solve the problems described above, the present invention provides a vacuum drying method for botulinum toxin, comprising the steps of: a first drying of a solution containing botulinum toxin at a temperature of 5° C. to 30° C. under a pressure of 0.01 to 2 mmHg; b) second drying of the first-dried product obtained in step a) at a temperature of 5° C. to 20° C. under a pressure of 0.01 to 1 mmHg; and c) third drying of the second-dried product obtained in step b) at a temperature of 5° C. to 30° C. under a pressure of 0.01 to 0.5 mmHg.

According to an aspect of the present invention, the step a) may be to perform first drying while the temperature is increased at 0.1° C./min to 2° C./min from an initial temperature of 5° C. or higher.

According to an aspect of the present invention, in the step a), an upper limit of the pressure may be 1.7 mmHg. In addition, according to a specific aspect of the present invention, in the step b), an upper limit of the pressure may be 0.8 mmHg. In addition, according to a specific aspect of the present invention, in the step c), an upper limit of the pressure may be 0.4 mmHg. According to a more specific aspect of the present invention, in the step c), an upper limit of the pressure may be 0.2 mmHg.

According to an aspect of the present invention, in each of the steps a), b), and c), drying time may be 30 minutes to 120 minutes.

According to a specific aspect of the present invention, in the vacuum drying method for botulinum toxin, total drying time may be 6 hours or less, more specifically, total drying time may be 5 hours or less, or total drying time may be 4 hours or less.

According to an aspect of the present invention, in the vacuum drying method for botulinum toxin, a titer recovery rate may be 80% or more, more specifically, a titer recovery rate may be 85% or more or 90% or more.

According to an aspect of the present invention, the botulinum toxin in the step a) is one or more selected from the group consisting of botulinum toxin types A, B, C1, C2, D, E, F, and G and botulinum serotypes.

According to an aspect of the present invention, a solution containing botulinum toxin in the step a) may include one or more selected from i) the group consisting of an excipient, a stabilizer, a preservative, a buffer, a thickener, a suspending agent, an emulsifier, a flavoring agent, a coloring agent, and a solubilizing agent; ii) the group consisting of sodium chloride, calcium chloride, sodium phosphate, calcium phosphate, sodium acetate, ethanol, propylene glycol, polyethylene glycol, and aqueous solutions thereof; and iii) the group consisting of albumin, gelatin, sugar, and sugar alcohol.

Advantageous Effects of Invention

The present invention relates to a vacuum drying method for botulinum toxin and has advantages that there is no need to adjust the temperature to below zero since the manufacturing is performed by vacuum drying, that drying is possible in a shorter period of time than in the related art, and that the overall yield is improved due to a high titer recovery rate. In addition, the botulinum toxin preparation manufactured including the drying method of the present invention is thin and hard and thus has advantages of providing strong impact resistance and excellent properties of the product.

DESCRIPTION OF EMBODIMENTS

Figure 1:
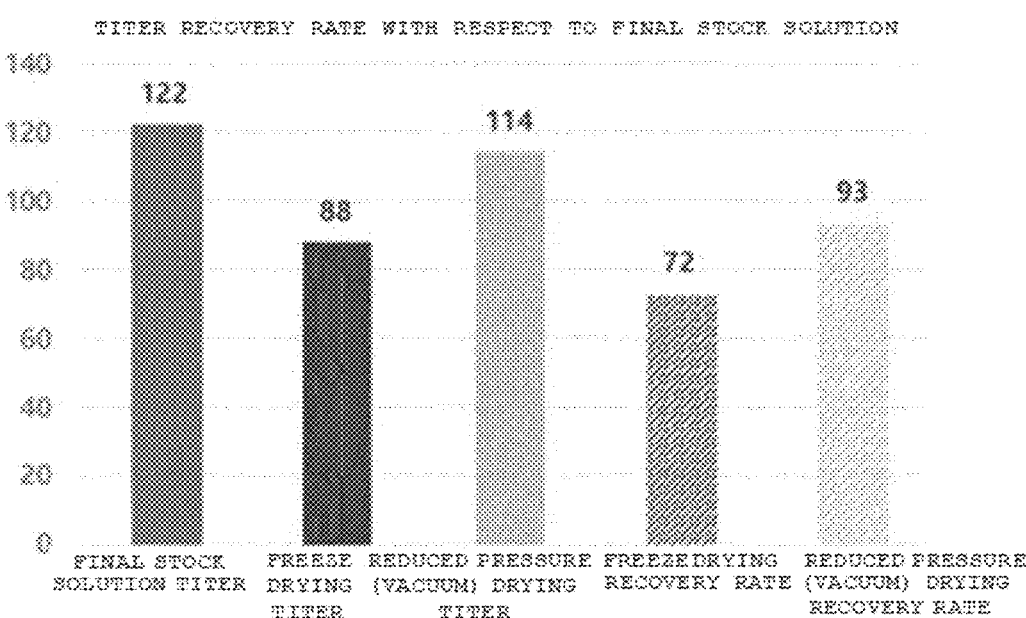
FIG. 1 is a diagram illustrating results obtained by measuring titer recovery rates according to drying methods of botulinum toxin.

The present invention relates to a vacuum drying method for botulinum toxin comprising the steps of: a) first drying of a solution containing botulinum toxin at a temperature of 5° C. to 30° C. under a pressure of 0.01 to 2 mmHg; b) a second drying of the first-dried product obtained in step a) at a temperature of 5° C. to 20° C. under a pressure of 0.01 to 1 mmHg; and c) final drying of the second-dried product obtained in step b) at a temperature of 5° C. to 30° C. under a pressure of 0.01 to 0.5 mmHg.

EMBODIMENTS

Hereinafter, the present invention is described in detail.

The present invention relates to a vacuum drying method for botulinum toxin comprising the steps of: a) first drying of solution containing botulinum toxin at a temperature of 5° C. to 30° C. under a pressure of 0.01 to 2 mmHg; b) second drying of the first-dried product obtained in step a) at a temperature of 5° C. to 20° C. under a pressure of 0.01 to 1 mmHg; and c) final drying of the second-dried product obtained in step b) at a temperature of 5° C. to 30° C. under a pressure of 0.01 to 0.5 mmHg.

Throughout the specification of the present invention, when a part "includes" a certain component, it means that other components may be further included rather than excluding other components, unless otherwise stated.

Numerical values such as an "upper limit", a "lower limit" and "X to Y" throughout the specification of the present invention mean including, not excluding, the corresponding numerical value.

In the present invention, the botulinum toxin is neurotoxic polypeptide produced by *Clostridium botulinum* and related species and includes not only a substance originally produced in the *Clostridium* genus but also substances produced by modification, recombination, and the like. In addition, unless otherwise defined, in the present invention, botulinum toxin includes all substances that can be recognized by those skilled in the art, and includes, but is not limited to, botulinum toxin types A, B, C1, C2, D, E, and the like. The botulinum toxin may be obtained by any known method or may be obtained commercially, and the method of obtaining is not particularly limited.

According to an aspect of the present invention, the botulinum toxin in the step a) is one or more selected from the group consisting of botulinum toxin types A, B, C1, C2, D, E, F, and G and botulinum serotypes.

According to an aspect of the present invention, the solution containing botulinum toxin in the step a) includes one or more selected from i) the group consisting of an excipient, a stabilizer, a preservative, a buffer, a thickener, a suspending agent, an emulsifier, a flavoring agent, a coloring agent, and a solubilizing agent; ii) the group consisting of sodium chloride, calcium chloride, sodium phosphate, calcium phosphate, sodium acetate, ethanol, propylene glycol, polyethylene glycol, and aqueous solutions thereof; and iii) the group consisting of albumin, gelatin, sugar, and sugar alcohol.

In the present invention, as additives, excipients, stabilizers, preservatives, buffers, thickeners, suspending agents, emulsifiers, flavoring agents, colorants, solubilizers, solvents, solubilizers, dispersants, disintegrants, plasticizers, lubricants, pain reliever agents, diluents, masking agents, and the like may be included. An additive is a material other than the pharmacologically active ingredient contained in the preparation and is used for additional purposes other than pharmacological activity, for example, additives to increase usability such as improvement of the stability and bioavailability of pharmaceutical compositions, or the like, additives to maintain formulation quality such as preservation or use of pharmaceutical compositions, additives to adjust the physical properties of pharmaceutical compositions, and the like. Also, additives can usually be used in a range that does not directly affect the pharmacological action.

For example, an excipient may be included to increase stability, and sodium hydrogen carbonate, sodium chloride, calcium phosphate, dextrin, and the like may be included as the excipient.

In addition, a solubilizing agent to increase the solubility of a material in a liquid phase may be included, and sodium salicylate, urea, monoethylacetamide, propylene glycol, dimethyl acetamide, hexamine, urethane, sodium acetate, and the like may be included as the solubilizing agent.

In addition, in order to prevent decomposition by acid, moisture, light, or the like, a stabilizer may be included, and nitrogen gas, carbon dioxide, sugar, sugar alcohol, human serum albumin, weak acids and salts thereof, weak bases and salts thereof, proteins, and the like may be included as the stabilizer. However, these are merely examples and the present invention is not limited thereto.

In the present invention, when the temperature of a step is below the upper limit, it is possible to form a stable preparation without destroying the active ingredient of the botulinum toxin.

According to a specific aspect of the present invention, the step a) may be to perform first drying while the temperature is increased at 0.1° C./min to 2° C./min from an initial temperature of 5° C. or higher. The initial temperature herein may be included in the above range.

Specifically, the step a) can be classified into 14 steps in maximum by changing the pressure conditions along with the increase of temperature. The first drying can be performed by varying not only the temperature and pressure but also the holding time at each stage.

According to a specific aspect of the present invention, the step a) proceeds in 14 steps in maximum while changing temperature, pressure, and time, and each step may be to perform first drying while selecting the increase of temperature in the range of 0.1° C./min to 2° C./min from the temperature of 5° C. to 30° C., the pressure in the range of 0.01 to 2 mmHg, and the time in the range of 0.1 to 40 minutes. More specifically, the step a) may proceed in 6 to 14 steps, 7 to 14 steps, 8 to 14 steps, 9 to 14 steps, or 10 to 14 steps while the temperature, the pressure, and the time are changed. In each step, the setting temperature may be increased sequentially. However, the pressure and the time do not necessarily increase or decrease sequentially.

In the present invention, the first drying is performed in 14 steps in maximum, and the temperature, the pressure, and the time are adjusted in each step, so that the active ingredient of the botulinum toxin may not be destroyed as much as possible. If the pressure and the temperature are set to be constant in four steps or less during first drying, a final stock solution of botulinum toxin is formed to be in a state in which internal and external portions are different, so that the active ingredient of the botulinum toxin becomes relatively low.

In a specific example, when the step a) proceeds in 10 steps, Steps 1 to 10 are sequentially performed. In Step 1, drying may be performed under the conditions of an initial set temperature of 5° C., a temperature increase rate of 0.1° C./min to 1° C./min, a pressure of 0.01 to 2 mmHg, and five minutes. In Step 2, drying may be performed under the conditions of a set temperature of 10° C., a temperature increase rate of 0.5° C./min, a pressure of 0.01 to 1.5 mmHg, and five minutes. In Step 3, drying may be performed under the conditions of a set temperature of 5° C., a temperature increase rate of 0.5° C./min, a pressure of 0.01 to 1.0 mmHg, and 10 minutes. In Step 4, drying may be performed under the conditions of a set temperature of 5° C., a temperature increase rate of 0.75° C./min, a pressure of 0.01 to 1.0 mmHg, and 20 minutes. In addition, in Step 5, drying may be performed under the conditions of a set temperature of 15° C., a temperature increase rate of 0.75° C./min, a pressure of 0.01 to 1.0 mmHg, and 10 minutes. In Steps 6, 7, 8, 9, and 10, each condition (temperature, a temperature increase rate, and pressure) may be the same as or lower than the condition in Step 5. However, these are merely examples and the present invention is not limited thereto.

According to an aspect of the present invention, the step a) proceeds in 10 to 14 steps while changing temperature, pressure, and time, and each step may be to perform first drying while selecting the increase of temperature in the range of 0.1° C./min to 1° C./min from the temperature of 5° C. to 30° C., the pressure in the range of 0.01 to 2 mmHg, and the time in the range of 0.1 to 30 minutes.

According to an aspect of the present invention, the step a) proceeds in 10 to 14 steps while changing temperature, pressure, and time, and each step may be to perform first drying while selecting the increase of temperature in the range of 0.1° C./min to 0.8° C./min from the temperature of 5° C. to 30° C., the pressure in the range of 0.01 to 2 mmHg, and the time in the range of 0.1 to 30 minutes.

More specifically, the step a) proceeds in 10 to 14 steps, and may be to perform first drying while selecting the increase of temperature in the range of 0.1° C./min to 1° C./min from the temperature of 5° C. to 10° C., the pressure in the range of 0.01 to 2 mmHg, and the time in the range of 5 to 20 minutes in Steps 1 to 4, and selecting the increase of temperature in the range of 0.1° C./min to 1° C./min from the temperature of 5° C. to 30° C., the pressure in the range of 0.01 to 1.7 mmHg, and the time in the range of 5 to 20 minutes in other steps.

More specifically, the step a) proceeds in 10 to 14 steps, and may be to perform first drying while selecting the increase of temperature in the range of 0.1° C./min to 0.5° C./min from the temperature of 5° C. to 20° C., the pressure in the range of 0.01 to 2 mmHg, and the time in the range of 5 to 20 minutes in Steps 1 to 3, selecting the increase of temperature in the range of 0.1° C./min to 0.5° C./min from the temperature of 5° C. to 20° C., the pressure in the range of 0.01 to 1 mmHg, and the time in the range of 5 to 20 minutes in Steps 4 to 7, and selecting the increase of temperature in the range of 0.1° C./min to 0.8° C./min from the temperature of 5° C. to 20° C., the pressure in the range of 0.01 to 0.5 mmHg, and the time in the range of 5 to 20 minutes in Steps 8 to 14.

According to an aspect of the present invention, the step b) proceeds in 2 steps while changing temperature, pressure, and time, and each step may be to perform second drying at the temperature in the range of 5° C. to 30° C., under the pressure in the range of 0.01 to 1 mmHg, and the time in the range of 0.1 to 80 minutes.

According to a specific aspect of the present invention, the step b) proceeds in 2 steps while changing temperature, pressure, and time, and each step may be to perform second drying at the temperature in the range of 20° C. to 30° C., under the pressure in the range of 0.05 to 1 mmHg, and the time in the range of 20 to 50 minutes.

In the present invention, the second drying proceeds in 2 steps to exhibit the same effect as that of the first drying.

According to an aspect of the present invention, the lower limit of the pressure in each step in the steps a), b), and c) may be 0.01 to 0.5 mmHg. According to a specific aspect of the present invention, the lower limit of the pressure in each of the steps may be 0.01, 0.05, 0.09, 0.13, 0.17, 0.20, 0.25, or 0.30 mmHg.

According to a specific aspect of the present invention, in the step a), the upper limit of the pressure may be 1.7 mmHg. According to a specific example of the present invention, the upper limit of the pressure in the step a) may be 1.6, 1.5, 1.4, 1.3, 1.2, 1.1, 1.05, or 1.0 mmHg.

In addition, according to a specific aspect of the present invention, in the step b), the upper limit of the pressure may be 0.6 to 2.0 mmHg. According to a specific aspect of the present invention, the upper limit of the pressure in the step b) may be 2.0, 1.5, 1.0, 0.8, 0.75, 0.7, or 0.6 mmHg.

In addition, according to a specific aspect of the present invention, in the step c), the upper limit of the pressure may be 0.4 mmHg. According to a specific example of the present invention, in the step c), the upper limit of the pressure may be 0.48, 0.45, 0.42, 0.40, 0.38, 0.35, 0.32, 0.30, 0.28, 0.25, 0.22, 0.20, or 0.10 mmHg.

In the present invention, when vacuum drying is performed in the above pressure range in each step, the purity of botulinum toxin is not degraded, and botulinum toxin with a higher purity can be provided. When botulinum toxin is administered by a method such as a procedure administered to the human body, the botulinum toxin is generally maintained for about 3 months and thus repeated administration is required. As a result, tolerance problems due to antibody formation in the body and stability problems due to high dose administration may occur. However, in the case of the vacuum drying method according to the present invention, vacuum drying is performed within the above pressure range to achieve high purity, and thus a valid effect may be exhibited even with a low dosage.

In addition, in the present invention, when vacuum drying is performed in the above pressure range, when manufacturing a botulinum toxin preparation, properties exhibit in thin and hard form, and thus shows impact resistance.

According to an aspect of the present invention, in the steps a), b), and c), the drying time in each step may be 30 minutes to 120 minutes.

According to a more specific aspect of the present invention, the drying time in the step b) may be 50 to 80 minutes.

According to a more specific aspect of the present invention, the drying time in the step c) may be 40 to 100 minutes.

According to a specific aspect of the present invention, the vacuum drying method for the botulinum toxin may have a total drying time of 6 hours or less. According to a specific example of the present invention, the total drying time of the vacuum drying method for the botulinum toxin may be 5 hours, 4.8 hours, 4.5 hours, 4.2 hours, or 4 hours or less.

In the present invention, the specific drying time may be adjusted in the above temperature and pressure range in consideration of minimizing the loss of botulinum toxin, forming a stable formulation, and manufacturing efficiency. In addition, in the present invention, the drying time is significantly shortened compared to the minimum of 18 hours, which is the drying time according to the freeze drying method of botulinum toxin in the related art, and thus an excellent effect is exhibited in terms of manufacturing efficiency.

The total drying time in the vacuum drying method for botulinum toxin according to the present invention means the entire time required for drying including the time for the first drying in the step a), the second drying in the step b), and the final drying in the step c) and does not mean the time required for the entire manufacturing of a botulinum toxin preparation. In the present invention, the total drying time is shortened by using the vacuum drying method, thereby increasing the manufacturing efficiency of the botulinum toxin preparation.

According to an aspect of the present invention, in the drying method for the botulinum toxin, the titer recovery rate may be 80% or more. A specific titer recovery rate may be 85% or more, 86% or more, 87% or more, 88% or more, 89% or more, or 90% or more. In the present invention, the titer recovery rate is expressed as the recovery rate by calculating titer of a final stock solution, a finished product by vacuum drying, and a finished product by freeze drying, and comparing the titer of the finished product by vacuum drying and the finished product by freeze drying in terms of 100% of the titer of the final stock solution.

Titer Recovery Rate of Finished Product by Freeze Drying (%)=Average Value of Titer of Finished Product by Freeze Drying/Average Value of Titer of Final Stock Solution×100

Titer Recovery Rate of Finished Product by Vacuum Drying (%)=Average Value of Titer of Finished Product by Vacuum Drying/Average Value of Titer of Final Stock Solution×100

The present invention has a high titer recovery rate and thus a loss of botulinum toxin protein during the manufacturing of a botulinum toxin preparation is small, so that even in the case of low-dose administration, the therapeutic or cosmetic effect of the active ingredient of the botulinum toxin can be effectively exhibited.

EXAMPLES

Hereinafter, the present invention is described in detail by way of examples and experimental examples.

However, the following examples and experimental examples are merely provided to exemplify the present invention, and the content of the present invention is not limited to the following examples and experimental examples.

<Example 1> Final Stock Solution of Botulinum Toxin

For the final stock solution of botulinum toxin, *Clostridium botulinum* toxin type A, sodium chloride as an excipient, and human serum albumin as a stabilizer were used. The specific composition is as shown in Table 1. The final stock solution was prepared at 500 ml, and a preparation target of the final stock solution was 100 to 120 units/0.1 mL in consideration of the loss.

TABLE 1

| Name of Raw Material | Reference Amount per Vial | Usage (based on 500 ml) |
|---|---|---|
| Stock Solution of Botulinum Toxin | 100 units | 100 to 120 units/0.1 mL |
| Sodium Chloride | 0.9 mg | 4.5 g |
| Human Serum Albumin | 0.5 mg | 2.5 g |

<Example 2> Vacuum Drying Method of Botulinum Toxin

A finished product was manufactured by vacuum drying of the final stock solution of botulinum toxin of <Example 1>. A vial was filled with the final stock solution of botulinum toxin of <Example 1> and half-stopped with a rubber stopper, and the vial filled with the final stock solution of botulinum toxin was loaded in the freeze dryer.

After that, a drying preparation step, first drying, second drying, and third drying were performed for drying, and each step was proceeded by varying temperature and pressure. The ranges of temperature and pressure in each step were as follows.

For drying preparation, the shelf temperature of the freeze dryer was maintained in the range of 5° C. to 30° C. for 0 to 10 minutes or longer. Thereafter, drying was started by setting the shelf temperature of the freeze dryer to the temperature of 5° C. to 30° C. and the minimum chamber pressure in the range of 0.01 to 2 mmHg.

First drying was performed in 14 steps in maximum while maintaining chamber pressure in the range of 0.01 to 2 mmHg and shelf temperature in the range of 5° C. to 30° C. (increase rate: at least 0.1° C./min to 0.5° C./min) for 0 to 40 minutes in each step.

Second drying was performed in at least 2 steps while maintaining chamber pressure in the range of 0.01 to 1 mmHg and shelf temperature in the range of 5° C. to 20° C. for 0 to 80 minutes in each step.

Final third drying was performed in 1 step while maintaining chamber pressure in the range of 0.01 to 0.5 mmHg and shelf temperature in the range of 5° C. to 30° C. for at least 30 minutes.

Figure 2:
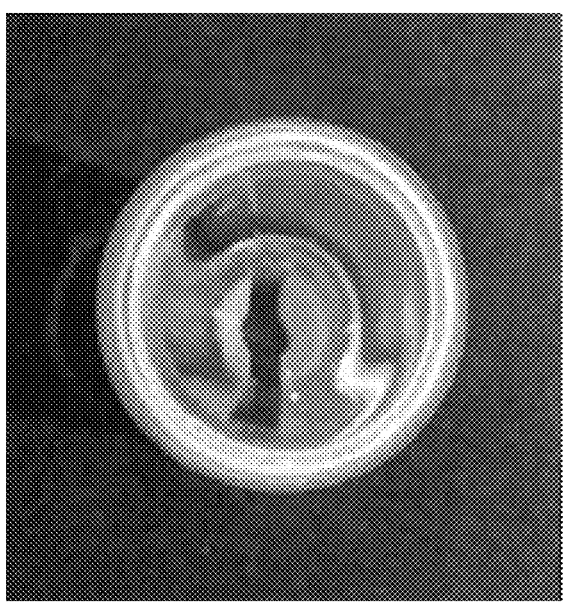
FIG. 2 is a diagram illustrating a formulation of a finished product manufactured by vacuum drying of botulinum toxin.

After drying was completed, stopping was performed with a rubber stopper while maintaining −0.3 to −0.7 bar using $N_2$ gas, and then the vacuum was released. Then, the dried vial was discharged from the freeze dryer shelf, sealed by aluminum cap sealing, and stored in refrigeration conditions. The shape of the finished product manufactured according to <Example 2> was as shown in FIG. 2.

<Example 2-1> Vacuum Drying of Botulinum Toxin (1)

A finished product was manufactured by vacuum drying of the final stock solution of botulinum toxin of <Example 1>. A vial was filled with the final stock solution of botulinum toxin of <Example 1> and half-stopped with a rubber stopper, the vial filled with the final stock solution of botulinum toxin was loaded in the freeze dryer, and then the shelf temperature of the freeze dryer was set 5° C. to 10° C. and maintained for 10 minutes. After that, drying was started by maintaining the shelf temperature of the freeze dryer at 5° C. to 10° C. and setting the chamber pressure to 0.1 mmHg.

First drying was proceeded by dividing temperature and pressure in 10 steps and performed under the conditions of Table 2 below.

TABLE 2

| Step | Temperature | Temperature Increase Rate | Pressure | Time |
|---|---|---|---|---|
| 1 | 5° C. | 0.5° C./min | 0.1 mmHg | 10 minutes |
| 2 | 5° C. | 0.3° C./min | 0.5 mmHg | 15 minutes |
| 3 | 5° C. | 0.3° C./min | 0.7 mmHg | 15 minutes |
| 4 | 5° C. | 0.4° C./min | 0.7 mmHg | 10 minutes |
| 5 | 15° C. | 0.4° C./min | 0.1 mmHg | 10 minutes |
| 6 | 15° C. | 0.4° C./min | 0.2 mmHg | 5 minutes |
| 7 | 15° C. | 0.8° C./min | 0.2 mmHg | 5 minutes |
| 8 | 15° C. | 0.8° C./min | 0.3 mmHg | 5 minutes |
| 9 | 15° C. | 0.8° C./min | 0.3 mmHg | 10 minutes |
| 10 | 20° C. | 0.3° C./min | 0.4 mmHg | 10 minutes |

Second drying was proceeded in 2 steps, and the second drying was performed i) by setting the chamber pressure of 0.5 mmHg and the shelf temperature of 20° C. and maintaining the setting for 25 minutes, and ii) by setting the chamber pressure of 0.3 mmHg and the shelf temperature of 20° C. and maintaining the setting for 25 minutes.

Third drying was performed for 40 minutes or more by setting the chamber pressure of 0.01 mmHg and the shelf temperature of 30° C. to complete the drying.

After the drying was completed, stopping was performed with a rubber stopper while maintaining −0.3 to −0.7 bar using N$_2$ gas, and then the vacuum was released. Then, the dried vial was discharged from the freeze dryer shelf, sealed by aluminum cap sealing, and stored in refrigeration conditions.

<Example 2-2> Vacuum Drying of Botulinum Toxin (2)

Vacuum drying was performed in the same method as in <Example 2-1>, except that the temperature and pressure of first drying, second drying, and third drying were different.

The first drying was performed by dividing the temperature and the pressure in 13 steps, and first drying was performed under the conditions of Table 3 below.

TABLE 3

| Step | Temperature | Temperature Increase Rate | Pressure | Time |
|---|---|---|---|---|
| 1 | 5° C. | 0.5° C./min | 0.1 mmHg | 5 minutes |
| 2 | 5° C. | 0.3° C./min | 1.5 mmHg | 15 minutes |
| 3 | 5° C. | 0.3° C./min | 1.8 mmHg | 10 minutes |
| 4 | 5° C. | 0.5° C./min | 1 mmHg | 5 minutes |
| 5 | 15° C. | 0.5° C./min | 0.8 mmHg | 5 minutes |
| 6 | 15° C. | 0.5° C./min | 0.7 mmHg | 10 minutes |
| 7 | 15° C. | 0.5° C./min | 0.3 mmHg | 10 minutes |
| 8 | 15° C. | 0.5° C./min | 0.4 mmHg | 10 minutes |
| 9 | 15° C. | 0.5° C./min | 0.5 mmHg | 15 minutes |
| 10 | 20° C. | 0.3° C./min | 0.5 mmHg | 5 minutes |
| 11 | 20° C. | 0.3° C./min | 0.4 mmHg | 5 minutes |
| 12 | 20° C. | 0.3° C./min | 0.3 mmHg | 10 minutes |
| 13 | 20° C. | 0.3° C./min | 0.3 mmHg | 10 minutes |

Second drying was proceeded in 2 steps, and the second drying was performed i) by setting the chamber pressure of 0.5 mmHg and the shelf temperature of 10° C. and maintaining the setting for 25 minutes, and ii) by setting the chamber pressure of 0.35 mmHg and the shelf temperature of 10° C. and maintaining the setting for 25 minutes.

Third drying was performed for 40 minutes or more by setting the chamber pressure of 0.01 mmHg and the shelf temperature of 25° C. to complete the drying.

<Example 2-3> Vacuum Drying of Botulinum Toxin (3)

Vacuum drying was performed in the same method as in <Example 2-1> except that the temperature and pressure of first drying, second drying, and third drying were different.

The first drying was performed by dividing the temperature and the pressure in 14 steps, and first drying was performed under the conditions of Table 4 below.

TABLE 4

| Step | Temperature | Temperature Increase Rate | Pressure | Time |
|---|---|---|---|---|
| 1 | 5° C. | 0.5° C./min | 0.1 mmHg | 5 minutes |
| 2 | 5° C. | 0.4° C./min | 0.5 mmHg | 10 minutes |
| 3 | 5° C. | 0.4° C./min | 1 mmHg | 10 minutes |
| 4 | 5° C. | 0.5° C./min | 0.5 mmHg | 10 minutes |
| 5 | 15° C. | 0.5° C./min | 0.8 mmHg | 5 minutes |
| 6 | 15° C. | 0.5° C./min | 0.9 mmHg | 5 minutes |
| 7 | 15° C. | 0.5° C./min | 1 mmHg | 5 minutes |
| 8 | 15° C. | 0.5° C./min | 0.3 mmHg | 10 minutes |
| 9 | 15° C. | 0.5° C./min | 0.4 mmHg | 10 minutes |
| 10 | 25° C. | 0.3° C./min | 0.5 mmHg | 5 minutes |
| 11 | 25° C. | 0.3° C./min | 0.2 mmHg | 5 minutes |
| 12 | 25° C. | 0.3° C./min | 0.3 mmHg | 5 minutes |
| 13 | 25° C. | 0.3° C./min | 0.4 mmHg | 10 minutes |
| 14 | 25° C. | 0.3° C./min | 0.5 mmHg | 10 minutes |

Second drying was proceeded in 2 steps, and the second drying was performed i) by setting the chamber pressure of 0.5 mmHg and the shelf temperature of 15° C. and maintaining the setting for 25 minutes, and ii) by setting the chamber pressure of 0.35 mmHg and the shelf temperature of 15° C. and maintaining the setting for 30 minutes.

Third drying was performed for 40 minutes or more at the chamber pressure of 0.01 mmHg and the shelf temperature of 30° C. to complete the drying.

<Example 2-4> Vacuum Drying of Botulinum Toxin (4)

Vacuum drying was performed in the same method as in <Example 2-1>, except that the temperature and pressure of first drying, second drying, and third drying were different.

The first drying was performed by dividing the temperature and the pressure in 10 steps, and first drying was performed under the conditions of Table 5 below.

TABLE 5

| Step | Temperature | Temperature Increase Rate | Pressure | Time |
|---|---|---|---|---|
| 1 | 5° C. | 0.5° C./min | 0.1 mmHg | 5 minutes |
| 2 | 5° C. | 0.3° C./min | 0.5 mmHg | 5 minutes |
| 3 | 5° C. | 0.3° C./min | 0.6 mmHg | 10 minutes |
| 4 | 5° C. | 0.5° C./min | 0.7 mmHg | 20 minutes |
| 5 | 15° C. | 0.5° C./min | 0.8 mmHg | 10 minutes |
| 6 | 15° C. | 0.5° C./min | 0.9 mmHg | 10 minutes |
| 7 | 15° C. | 0.5° C./min | 1 mmHg | 10 minutes |
| 8 | 15° C. | 0.5° C./min | 0.3 mmHg | 15 minutes |
| 9 | 20° C. | 0.3° C./min | 0.4 mmHg | 15 minutes |
| 10 | 20° C. | 0.3° C./min | 0.5 mmHg | 5 minutes |

Second drying was proceeded in 2 steps, and the second drying was performed i) by setting the chamber pressure of 0.5 mmHg and the shelf temperature of 15° C. and maintaining the setting for 30 minutes, and ii) by setting the chamber pressure of 0.4 mmHg and the shelf temperature of 15° C. and maintaining the setting for 30 minutes.

Third drying was performed for 40 minutes or more at the chamber pressure of 0.01 mmHg and the shelf temperature of 30° C. to complete the drying.

<Example 2-5> Vacuum Drying of Botulinum Toxin (5)

Vacuum drying was performed in the same method as in <Example 2-1>, except that the temperature and pressure of drying preparation, first drying, second drying, and third drying were different.

The shelf temperature of the freeze dryer was set to 0° C. to 5° C., and the setting was maintained for 10 minutes. Thereafter, drying was started by maintaining the shelf temperature of the freeze dryer at 0° C. to 5° C. and setting the chamber pressure was set to 1.6 mmHg.

The first drying was performed by dividing the temperature and the pressure in 11 steps, and first drying was performed under the conditions of Table 6 below.

TABLE 6

| Step | Temperature | Temperature Increase Rate | Pressure | Time |
|---|---|---|---|---|
| 1 | 5° C. | 0.3° C./min | 1.6 mmHg | 5 minutes |
| 2 | 5° C. | 0.3° C./min | 1.6 mmHg | 5 minutes |
| 3 | 5° C. | 0.3° C./min | 1.4 mmHg | 10 minutes |
| 4 | 5° C. | 0.4° C./min | 1.2 mmHg | 10 minutes |
| 5 | 15° C. | 0.4° C./min | 1.2 mmHg | 5 minutes |
| 6 | 15° C. | 0.4° C./min | 1.0 mmHg | 5 minutes |
| 7 | 15° C. | 0.4° C./min | 1.0 mmHg | 10 minutes |
| 8 | 15° C. | 0.8° C./min | 0.5 mmHg | 15 minutes |
| 9 | 15° C. | 0.8° C./min | 0.4 mmHg | 5 minutes |
| 10 | 20° C. | 0.3° C./min | 0.3 mmHg | 15 minutes |
| 11 | 20° C. | 0.3° C./min | 0.1 mmHg | 20 minutes |

Second drying was proceeded in 2 steps, and the second drying was performed i) by setting the chamber pressure of 0.3 mmHg and the shelf temperature of 20° C. and maintaining the setting for 25 minutes, and ii) by setting the chamber pressure of 0.4 mmHg and the shelf temperature of 20° C. and maintaining the setting for 25 minutes.

Third drying was performed for 40 minutes or more at the chamber pressure of 0.01 mmHg and the shelf temperature of 30° C. to complete the drying.

<Example 2-6> Vacuum Drying of Botulinum Toxin (6)

Vacuum drying was performed in the same method as in <Example 2-1>, except that the temperature and pressure of drying preparation, first drying, second drying, and third drying were different.

The shelf temperature of the freeze dryer was set to 0° C. to 5° C., and the setting was maintained for 10 minutes. Thereafter, drying was started by maintaining the shelf temperature of the freeze dryer at 0° C. to 5° C. and setting the chamber pressure was set to 1.6 mmHg.

The first drying was performed by dividing the temperature and the pressure in 14 steps, and first drying was performed under the conditions of Table 7 below.

TABLE 7

| Step | Temperature | Temperature Increase Rate | Pressure | Time |
|---|---|---|---|---|
| 1 | 5° C. | 0.4° C./min | 1.6 mmHg | 5 minutes |
| 2 | 5° C. | 0.4° C./min | 1.0 mmHg | 5 minutes |
| 3 | 5° C. | 0.5° C./min | 0.8 mmHg | 10 minutes |
| 4 | 5° C. | 0.5° C./min | 0.5 mmHg | 20 minutes |
| 5 | 10° C. | 0.4° C./min | 1 mmHg | 5 minutes |
| 6 | 10° C. | 0.4° C./min | 0.9 mmHg | 5 minutes |
| 7 | 10° C. | 0.5° C./min | 0.8 mmHg | 5 minutes |
| 8 | 10° C. | 0.5° C./min | 0.5 mmHg | 10 minutes |
| 9 | 15° C. | 0.3° C./min | 0.5 mmHg | 5 minutes |
| 10 | 15° C. | 0.3° C./min | 0.4 mmHg | 5 minutes |
| 11 | 15° C. | 0.3° C./min | 0.3 mmHg | 10 minutes |
| 12 | 15° C. | 0.3° C./min | 0.2 mmHg | 10 minutes |
| 13 | 20° C. | 0.3° C./min | 0.2 mmHg | 5 minutes |
| 14 | 20° C. | 0.3° C./min | 0.1 mmHg | 10 minutes |

Second drying was proceeded in 2 steps, and the second drying was performed i) by setting the chamber pressure of 0.35 mmHg and the shelf temperature of 20° C. and maintaining the setting for 25 minutes, and ii) by setting the chamber pressure of 0.5 mmHg and the shelf temperature of 20° C. and maintaining the setting for 25 minutes.

Third drying was performed for 40 minutes or more at the chamber pressure of 0.01 mmHg and the shelf temperature of 30° C. to complete the drying.

<Example 2-7> Vacuum Drying of Botulinum Toxin (7)

Vacuum drying was performed in the same method as in <Example 2-1>, except that temperature and pressure of drying preparation, first drying, second drying, and third drying were different.

The shelf temperature of the freeze dryer was set to 0° C. to 5° C., and the setting was maintained for 10 minutes. Thereafter, drying was started by maintaining the shelf temperature of the freeze dryer at 0° C. to 5° C. and setting the chamber pressure was set to 1.6 mmHg.

The first drying was performed by dividing the temperature and the pressure in 10 steps, and first drying was performed under the conditions of Table 8 below.

TABLE 8

| Step | Temperature | Temperature Increase Rate | Pressure | Time |
|---|---|---|---|---|
| 1 | 5° C. | 0.5° C./min | 1.6 mmHg | 5 minutes |
| 2 | 5° C. | 0.3° C./min | 1.5 mmHg | 5 minutes |
| 3 | 5° C. | 0.3° C./min | 1 mmHg | 10 minutes |

TABLE 8-continued

| Step | Temperature | Temperature Increase Rate | Pressure | Time |
|---|---|---|---|---|
| 4 | 5° C. | 0.3° C./min | 0.9 mmHg | 15 minutes |
| 5 | 10° C. | 0.5° C./min | 0.8 mmHg | 5 minutes |
| 6 | 10° C. | 0.5° C./min | 0.7 mmHg | 10 minutes |
| 7 | 10° C. | 0.5° C./min | 0.6 mmHg | 10 minutes |
| 8 | 10° C. | 0.5° C./min | 0.5 mmHg | 10 minutes |
| 9 | 15° C. | 0.5° C./min | 0.4 mmHg | 15 minutes |
| 10 | 15° C. | 0.5° C./min | 0.1 mmHg | 20 minutes |

Second drying was proceeded in 2 steps, and the second drying was performed i) by setting the chamber pressure of 0.4 mmHg and the shelf temperature of 15° C. and maintaining the setting for 25 minutes, and ii) by setting the chamber pressure of 0.5 mmHg and the shelf temperature of 15° C., and maintaining the setting for 25 minutes.

Third drying was performed for 40 minutes or more at the chamber pressure of 0.01 mmHg and the shelf temperature of 25° C. to complete the drying.

<Example 2-8> Vacuum Drying of Botulinum Toxin (8)

Vacuum drying was performed in the same method as in <Example 2-1>, except that the temperature and pressure of drying preparation, first drying, second drying, and third drying were different.

The shelf temperature of the freeze dryer was set to 0° C. to 5° C., and the setting was maintained for 10 minutes. Thereafter, drying started by maintaining the shelf temperature of the freeze dryer at 0° C. to 5° C. and setting the chamber pressure to 1.6 mmHg.

The first drying was performed by dividing the temperature and the pressure in 12 steps, and first drying was performed under the conditions of Table 9 below.

TABLE 9

| Step | Temperature | Temperature Increase Rate | Pressure | Time |
|---|---|---|---|---|
| 1 | 5° C. | 0.3° C./min | 1.6 mmHg | 5 minutes |
| 2 | 5° C. | 0.3° C./min | 1.5 mmHg | 5 minutes |
| 3 | 5° C. | 0.3° C./min | 1.0 mmHg | 10 minutes |
| 4 | 5° C. | 0.3° C./min | 1.0 mmHg | 5 minutes |
| 5 | 10° C. | 0.3° C./min | 0.9 mmHg | 5 minutes |
| 6 | 10° C. | 0.5° C./min | 0.8 mmHg | 10 minutes |
| 7 | 10° C. | 0.5° C./min | 0.5 mmHg | 10 minutes |
| 8 | 15° C. | 0.8° C./min | 0.5 mmHg | 5 minutes |
| 9 | 15° C. | 0.8° C./min | 0.4 mmHg | 5 minutes |
| 10 | 20° C. | 0.3° C./min | 0.3 mmHg | 10 minutes |
| 11 | 20° C. | 0.3° C./min | 0.2 mmHg | 10 minutes |
| 12 | 20° C. | 0.3° C./min | 0.1 mmHg | 15 minutes |

Second drying was proceeded in 2 steps, and the second drying was performed i) by setting the chamber pressure of 0.4 mmHg and the shelf temperature of 15° C. and maintaining the setting for 30 minutes, and ii) by setting the chamber pressure of 0.5 mmHg and the shelf temperature of 15° C., and maintaining the setting for 30 minutes.

Third drying was performed for 40 minutes or more at the chamber pressure of 0.01 mmHg and the shelf temperature of 25° C. to complete the drying.

<Example 2-9> Vacuum Drying of Botulinum Toxin (9)

Vacuum drying was performed in the same method as in <Example 2-1>, except that the temperature and pressure of drying preparation, first drying, second drying, and third drying were different.

The shelf temperature of the freeze dryer was set to 0° C. to 5° C., and the setting was maintained for 10 minutes. Thereafter, drying was started by maintaining the shelf temperature of the freeze dryer at 0° C. to 5° C. and setting the chamber pressure to 1.6 mmHg.

The first drying was performed by dividing the temperature and the pressure in 14 steps, and first drying was performed under the conditions of Table 10 below.

TABLE 10

| Step | Temperature | Temperature Increase Rate | Pressure | Time |
|---|---|---|---|---|
| 1 | 10° C. | 0.1° C./min | 1.0 | 5 minutes |
| 2 | 20° C. | 0.2° C./min | 0.9 mmHg | 5 minutes |
| 3 | 20° C. | 0.2° C./min | 0.8 mmHg | 10 minutes |
| 4 | 20° C. | 0.2° C./min | 0.1 mmHg | 5 minutes |
| 5 | 20° C. | 0.2° C./min | 0.2 mmHg | 5 minutes |
| 6 | 20° C. | 0.2° C./min | 0.3 mmHg | 10 minutes |
| 7 | 20° C. | 0.2° C./min | 0.4 mmHg | 10 minutes |
| 8 | 20° C. | 0.5° C./min | 0.1 mmHg | 5 minutes |
| 9 | 20° C. | 0.5° C./min | 0.15 mmHg | 5 minutes |
| 10 | 20° C. | 0.5° C./min | 0.2 mmHg | 10 minutes |
| 11 | 25° C. | 0.5° C./min | 0.1 mmHg | 10 minutes |
| 12 | 25° C. | 0.6° C./min | 0.2 mmHg | 10 minutes |
| 13 | 25° C. | 0.7° C./min | 0.2 mmHg | 10 minutes |
| 14 | 25° C. | 0.8° C./min | 0.2 mmHg | 10 minutes |

Second drying was proceeded in 2 steps, and the second drying was performed i) by setting the chamber pressure of 0.2 mmHg and the shelf temperature of 25° C. and maintaining the setting for 30 minutes, and ii) by setting the chamber pressure of 0.2 mmHg and the shelf temperature of 25° C. and maintaining the setting for 30 minutes.

Third drying was performed for 40 minutes or more at the chamber pressure of 0.05 mmHg and the shelf temperature of 25° C. to complete the drying.

<Comparative Example 1> Freeze Drying Method of Botulinum Toxin

A finished product was manufactured by freeze drying of a final stock solution of botulinum toxin of <Example 1>. A vial was filled with the final stock solution of botulinum toxin of <Example 1> and half-stopped with a rubber stopper. The shelf temperature of the freeze dryer was set 0° C. to 5° C., the vial filled with the final stock solution of botulinum toxin was loaded in the freeze dryer, and the shelf temperature of the freeze dryer was set to about −45° C. and maintained for 30 minutes. After that, drying was started by maintaining the shelf temperature of the freeze dryer at about −40° C. and setting the chamber pressure to 0.1 mmHg.

First drying was performed by setting the chamber pressure to about 10 mmHg and the shelf temperature to about −45° C. (increase rate: 1° C./4 minutes), and maintaining the setting for about 60 minutes. Second drying was performed by setting the chamber pressure to about 10 mmHg and the shelf temperature to about −10° C. (increase rate: 1° C./4 minutes), and maintaining the setting for about 30 minutes. After that, drying was performed for at least 10 hours with the chamber pressure of about 10 mmHg and the shelf temperature of about 30° C. (increase rate: at least 1° C./4 minutes) to complete drying.

Figure 3:
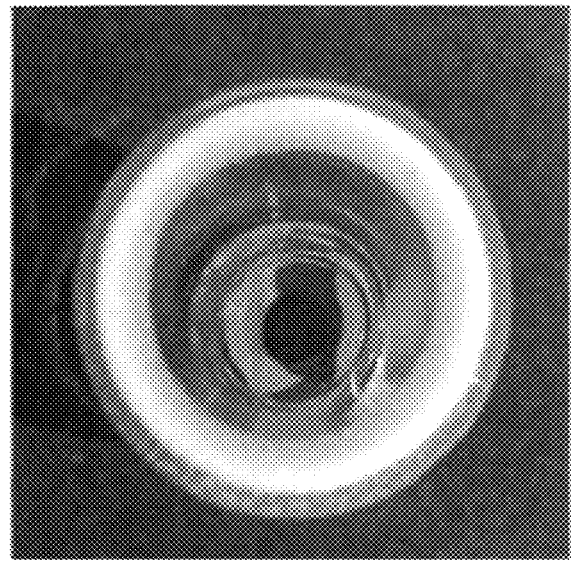
FIG. 3 is a diagram illustrating a formulation of a finished product manufactured by freeze drying of botulinum toxin.

After the drying was completed, the vacuum was released after stopping with a rubber stopper, and then the dried vial was discharged from the freeze dryer shelf, sealed by aluminum cap sealing, and stored in refrigeration conditions. The shape of the manufactured finished product was as shown in FIG. 3.

<Experimental Example 1> Animal Titer Test

<1-1> Measurement Method

In the method of measuring a recovery rate of a titer, the recovery rate is expressed by % by calculating titer of a final stock solution, a finished product by vacuum drying, and a finished product by freeze drying, and comparing the titer of the finished product by vacuum drying and the finished product by freeze drying with respect to the final stock solution in terms of 100% of the titer of the final stock solution. It was confirmed that, in the case of the titer of the finished product by freeze drying, the recovery rate of the titer (average value) of the finished product by freeze drying to the titer (average value) of the final stock solution was about 72%, and the recovery rate of the titer (average value) of the finished product by vacuum drying to the titer (average value) of the final stock solution corresponds to 93%.

Titer Recovery Rate of Finished Product by Freeze Drying (%)=Average Value of Titer of Finished Product by Freeze Drying/Average Value of Final Stock Solution Titer×100

Titer Recovery Rate of Finished Product by Vacuum Drying (%)=Average Value of Finished Product Titer by Vacuum Drying/Average Value of Final Stock Solution Titer×100

<1-2> Test Result

Table 11 shows results of an animal titer test performed three times on the final stock solution of <Example 1>, the finished product by vacuum drying of <Example 2>, and the finished product of freeze drying of <Comparative Example 1>.

TABLE 11

| | | Animal Titer Test Result | | | | |
|---|---|---|---|---|---|---|
| Classification | | First Time | Second Time | Third Time | Average | |
| Final Stock | Tester A | 123 | 129 | 132 | 128 | 122 |
| Solution | Tester B | 113 | 115 | 119 | 116 | |
| (units/0.1 ml) | | | | | | |
| Finished | Tester A | 110 | 115 | 123 | 116 | 114 |
| Product by | Tester B | 108 | 110 | 115 | 111 | |
| Vacuum Drying | | | | | | |
| (units/vial) | | | | | | |
| Finished | Tester A | 88 | 92 | 94 | 91 | 88 |
| Product by | Tester B | 83 | 83 | 87 | 85 | |
| Freeze Drying | | | | | | |
| (units/vial) | | | | | | |

As shown in Table 11, the result value of the animal titer test of the final stock solution was 113 units/0.1 ml in minimum, 132 units/0.1 ml in maximum, and 122 units/0.1 ml in average and was the preparation target of 100 units/0.1 mL±10% (100 to 120 units/0.1 mL) considering the preparation deviations and test deviations. Thus, it was confirmed that there is no error in the manufacturing process.

The animal titer test result of the finished product by freeze drying was 83 units/vial in minimum, 94 units/vial in maximum, and 86 units/vial in average, and the recovery rate with respect to the titer of the final stock solution was only 72%. The animal titer test result of the finished product by vacuum drying was 108 units/vial in minimum, 123 units/vial in maximum, and 114 units/vial in average, and it was confirmed that the recovery rate with respect to the titer of the final stock solution corresponds to 93%.

Therefore, it was confirmed that the titer recovery rate of the finished product manufactured by vacuum drying was about 21% higher than that of the finished product manufactured by freeze drying, confirming that the loss of botulinum toxin protein was small. In addition, as illustrated in FIG. 2, the properties of the finished product are thin and hard, and the impact resistance is strengthened, so the stability is high. In addition, compared to freeze drying, vacuum drying requires a very short period of time thereby being advantageous in terms of efficiency.

INDUSTRIAL APPLICABILITY

The present invention relates to the manufacturing of botulinum toxin and can be usefully used in the fields of medicine, cosmetics, and the like.

The invention claimed is:

1. A vacuum drying method for botulinum toxin comprising the steps of:
   a) first, drying a solution containing botulinum toxin at a temperature of 5° C. to 30° C. under a pressure of 0.09 to 2 mmHg while increasing the temperature at a rate of 0.1° C./min to 2° C./min from an initial temperature of 5° C. or higher;
   b) second, drying the first-dried product obtained in step a) at a temperature of 5° C. to 20° C. under a pressure of 0.09 to 1 mmHg; and
   c) third, drying the second-dried product obtained in step b) at a temperature of 5° C. to 30° C. under a pressure of 0.01 to 0.5 mmHg.

2. The vacuum drying method for botulinum toxin according to claim 1,
   wherein, in the step a), the upper limit of the pressure is 1.7 mmHg.

3. The vacuum drying method for botulinum toxin according to claim 1,
   wherein, in the step b), the upper limit of the pressure is 0.8 mmHg.

4. The vacuum drying method for botulinum toxin according to claim 1,
   wherein, in the step c), the upper limit of the pressure is 0.4 mmHg.

5. The vacuum drying method for botulinum toxin according to claim 1,
   wherein, in the step c), the upper limit of the pressure is 0.2 mmHg.

6. The vacuum drying method for botulinum toxin according to claim 1,
   wherein, in each of the steps a), b), and c), drying time is 30 minutes to 120 minutes.

7. The vacuum drying method for botulinum toxin according to claim 1,
   wherein, in the vacuum drying method for botulinum toxin, total drying time is 6 hours or less.

8. The vacuum drying method for botulinum toxin according to claim 1,
   wherein, in the vacuum drying method for botulinum toxin, total drying time is 5 hours or less.

9. The vacuum drying method for botulinum toxin according to claim 1, wherein, in the vacuum drying method for botulinum toxin, total drying time is 4 hours or less.

10. The vacuum drying method for botulinum toxin according to claim 1, wherein, the vacuum drying method for botulinum toxin achieves a titer recovery rate of 80% or more.

11. The vacuum drying method for botulinum toxin according to claim 1, wherein, the vacuum drying method for botulinum toxin achieves a titer recovery rate of 85% or more.

12. The vacuum drying method for botulinum toxin according to claim 1, wherein, the vacuum drying method for botulinum toxin achieves a titer recovery rate of 90% or more.

13. The vacuum drying method for botulinum toxin according to claim 1, wherein, the botulinum toxin in the step a) is one or more selected from the group consisting of botulinum toxin types A, B, C1, C2, D, E, F, and G and botulinum serotypes.

14. The vacuum drying method for botulinum toxin according to claim 1, wherein the solution containing botulinum toxin in the step a) includes one or more selected from i) the group consisting of an excipient, a stabilizer, a preservative, a buffer, a thickener, a suspending agent, an emulsifier, a flavoring agent, a coloring agent, and a solubilizing agent; ii) the group consisting of sodium chloride, calcium chloride, sodium phosphate, calcium phosphate, sodium acetate, ethanol, propylene glycol, polyethylene glycol, and aqueous solutions thereof; and iii) the group consisting of albumin, gelatin, sugar, and sugar alcohol.

\* \* \* \* \*